United States Patent [19]

Bare et al.

[11] 4,018,891

[45] Apr. 19, 1977

[54] PHARMACEUTICAL COMPOSITIONS AND METHODS OF TREATMENT WITH 1-OXO-1H-2-BENZOTHIO PYRAN-3-CARBOXYLIC ACID DERIVATIVES

[75] Inventors: Thomas M. Bare, Milwaukee; John T. Suh, Mequon, both of Wis.

[73] Assignee: Richardson-Merrell Inc., Wilton, Conn.

[22] Filed: Nov. 17, 1975

[21] Appl. No.: 632,241

Related U.S. Application Data

[62] Division of Ser. No. 485,378, July 3, 1974, Pat. No. 3,960,892.

[52] U.S. Cl. .................................. 424/275; 424/283
[51] Int. Cl.$^2$ ...................................... A61K 31/35
[58] Field of Search ........................... 424/275, 283

[56] References Cited

UNITED STATES PATENTS

| | | | |
|---|---|---|---|
| 3,008,970 | 11/1961 | van der Stelt | 260/343.2 |
| 3,804,857 | 4/1974 | Cairns et al. | 424/275 |
| 3,857,856 | 12/1974 | Cairns et al. | 424/275 |
| 3,952,013 | 4/1976 | Hazard et al. | 424/275 |

*Primary Examiner*—Norman A. Drezin
*Attorney, Agent, or Firm*—George W. Rauchfuss, Jr.; Eugene O. Retter; L. Ruth Hattan

[57] ABSTRACT

The method comprises administering to an animal a novel pharmaceutical composition containing a substituted-1-oxo-1H-2-benzothiopyran-3-carboxylic acid to inhibit antigen-antibody reaction in said animal. Representative of the compounds that can be used in the method are:

1-Oxo-1H-2-benzothiopyran-3-carboxylic acid, and
Sodium 6-methoxy-1-oxo-1H-2-benzothiopyran-3-carboxylate.

8 Claims, No Drawings

PHARMACEUTICAL COMPOSITIONS AND METHODS OF TREATMENT WITH 1-OXO-1H-2-BENZOTHIO PYRAN-3-CARBOXYLIC ACID DERIVATIVES

This is a division of application Ser. No. 485,378, filed July 3, 1974, and now U.S. Pat. No. 3,960,892 issued June 1, 1976.

BACKGROUND OF THE INVENTION

The compound disodium cromoglycate (Intal), which inhibits the release of spasmogens from antigen-antibody reactions, is effective in the treatment of asthma and other allergic diseases. Numerous articles have been published which report the clinical results obtained with disodium cromoglycate. In addition, the following U.S. Pats. have issued describing disodium cromoglycate and related compounds: Nos. 3,567,741; 3,706,768; 3,705,945; 3,419,578; 3,686,412; 3,671,625; 3,728,688; 3,673,218; 3,686,320; and 3,634,582. The compound 1-oxo-1H-2-benzothiopyran-3-carboxylic acid has been described by Dijksman and Newbold, J. Chem. Soc., 1951, 1213, and related compounds have been described by J. N. Chatterjea, et al., J. Indian Chem. Soc., 44, 697 (1967).

DESCRIPTION OF THE INVENTION

The present invention relates to a method of preventing allergic reactions in animals which comprises administering to said animals pharmaceutical compositions containing a compound of the formula:

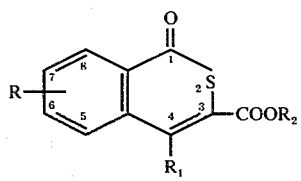

in which R is hydrogen or lower alkoxy of 1 to 4 carbon atoms, methoxy, isopropoxy and t-butoxy, $R_1$ is hydrogen or lower alkyl of 1 to 4 carbon atoms such as methyl, ethyl, isopropyl or butyl, and $R_2$ is hydrogen or sodium.

Representative of the compounds which may be employed in the method are the following:

1-Oxo-1H-2-benzothiopyran-3-carboxylic acid,
6-Methoxy-1-oxo-1H-2-benzothiopyran-3-carboxylic acid,
Sodium 1-oxo-1H-2-benzothiopyran-3-carboxylate,
Sodium 6-methoxy-1-oxo-1H-2-benzothiopyran-3-carboxylate,
7-Methoxy-1-oxo-1H-2-benzothiopyran-3-carboxylic acid,
8-Methoxy-1-oxo-1H-2-benzothiopyran-3-carboxylic acid,
4-Methyl-1-oxo-1H-2-benzothiopyran-3-carboxylic acid,
8-Isopropoxy-1-oxo-1H-2-benzothiopyran-3-carboxylic acid, and
8-Tert-butoxy-1-oxo-1H-2-benzothiopyran-3-carboxylic acid.

The above compounds may be prepared as described in the examples or in a manner similar to that described in the previously mentioned publications.

The compounds inhibit the release of spasmogens from antigen-antibody reactions such as occur in rats during the PCA (passive cutaneous anaphylaxis) tests described by Ogilvie in *The Journal of Immunology*, Vol. 12, page 113 (1967). For example, the compound sodium 1-oxo-1H-2-benzothiopyran-3-carboxylic acid, when given intravenously and orally in doses of 80 mg/kg, was found to be as potent as disodium cromoglycate in inhibiting the PCA reaction induced by reaginic antibodies in sensitized rats. It has been found that this test gives reliable qualitative indications of the ability of the compounds being tested to inhibit antibody-antigen reactions in man. The compounds are surprisingly effective orally. Therefore, the compounds are of value in the treatment of conditions in which the extrinsic antigen combination with a reaginic antibody is primarily responsible, for example, extrinsic asthma, hay fever, urticaria, eczema or atopic dermatitis.

In animal behavior tests sodium 1-oxo-1H-2-benzothiopyran-3-carboxylic acid was found to possess a very low toxicity, that is, it had an oral $LD_{50}$ value of at least 500 mg/kg of the compound in terms of the free acid.

The inventive method is preferably carried out employing the active ingredient in the form of a pharmaceutical composition which contains, in addition, suitable pharmaceutical carriers and excipients. The compositions may also contain other medicinal agents such as bronchodilators, antihistamines or tranquilizers. Suitable dosage forms include tablets, capsules, syrups, emulsions and powders for inhalation.

The preferred form of administration is by oral administration. Tablets or capsules containing the active ingredients plus pharmaceutical diluents can be prepared by conventional techniques. In addition, the compounds may be administered by inhalaltion. Compositions employed for inhalation will generally be in the form of a powder or an aerosol spray. The following are representative formulations for inhalaltion:

| Aerosol Formulation | |
|---|---|
| Sodium 1-oxo-1H-2-benzothiopyran-3-carboxylate | 2% |
| Sodium dioctyl sulphosuccinate | 0.004% |
| Propellant | ad 100% |

| Solid Powder Formulation | |
|---|---|
| Each dosage unit contains: | |
| Sodium 1-oxo-1H-2-benzothiopyran-3-carboxylate | 20 mg. |
| Lactose | 15 mg. |

The dosage at which the active ingredient is administered may vary within a wide range depending upon the physical condition of the patient and the allergic reaction being treated. Generally, however, a suitable oral dosage range is from 20 to 1500 mg. and a suitable inhalation dosage range is from 1 to 50 mg.

The following examples further illustrate the invention:

EXAMPLE 1

5-o-Carboxybenzylidenerhodanine

To a hot stirred solution of 20.5 g. (134 mM) of phthalaldehydic acid and 17.95 g. (135 mM) of rhodanine in 90 ml. of glacial acetic acid is added 36.0 g. (438 mM) of sodium acetate. While heating the resulting solution to reflux, a precipitate forms and an additional 30 ml. of acetic acid is added. After refluxing the mixture for 0.5 hour, it is cooled, poured into water, and filtered to separate a yellow solid. The solid is washed with water and boiled with 500 ml. of isopropanol. The resulting mixture is cooled and filtered to separate 31.14 g. (87.5%) of the 5-o-carboxybenzylidenerhodanine as yellow needles, m.p. 276°–278°.

EXAMPLE 2

1-Oxo-1H-2-benzothiopyran-3-carboxylic acid

A mixture of 31.00 g. (117 mM) of the benzylidenerhodanine of Example 1 and 230 ml. of 15% aqueous sodium hydroxide is refluxed for 30 minutes. The solution is cooled, poured into excess cold, dilute hydrochloric acid, and filtered. The collected solid is recrystallized from 200 ml. of ethanol to give 11.74 g. (57.1%) of 1-oxo-1H-2-benzothiopyran-3-carboxylic acid as pale yellow needles, m.p. 260°–262°.

Anal. Calcd. for $C_{10}H_6O_3S$: C, 58.24; H, 2.94; S, 15.55. Found: C, 58.27; H, 2.96; S, 15.65.

EXAMPLE 3

Sodium 1-oxo-1H-2-benzothiopyran-2-carboxylate

To a stirred suspension of 4.50 g. (21.8 mM) of the carboxylic acid of Example 2 in 200 ml. of distilled water is added 1.833 g. (21.82 mM) of sodium bicarbonate. The mixture is then stirred at 25°–35° for 2 hours, whereupon all the solids dissolve. The solution is frozen and freeze-dried to give sodium 1-oxo-1H-2-benzothiopyran-2-carboxylate as a pale yellow solid, m.p. >350°.

Anal. Calcd. for $C_{10}H_5O_3SNa$: C, 52.63; H, 2.21; S, 14.05. Found: C, 52.39; H, 2.39; S, 13.98.

EXAMPLE 4

5-(2-Carboxy-5-methoxybenzylidene)rhodanine

To a stirred hot solution of 4.23 g. (23.5 mM) of 4-methoxyphthalaldehydic acid and 3.13 g. (23.5 mM) of rhodanine in 16.5 ml. of acetic acid is added 6.33 g. (77.2 mM) of anhydrous sodium acetate. The resulting hot solution is refluxed for 0.5 hour, whereupon a solid yellow mass forms. The mixture is cooled, poured into water, to yield 5-(2-carboxy-5-methoxybenzylidene)rhodanine.

EXAMPLE 5

6-Methoxy-1-oxo-1H-2-benzothiopyran-3-carboxylic acid

A solution of the 5-(2-carboxy-5-methoxybenzylidene)rhodanine of Example 4 in dilute sodium hydroxide (35 ml. of 20% NaOH + 11 ml. $H_2O$) is refluxed for one hour and then poured into dilute HCl. The resulting pale yellow solid is collected and recrystallized repeatedly from ethanol to give 6-methoxy-1-oxo-1H-2-benzothiopyran-3-carboxylic acid as pale yellow crystals, m.p. 278°–279°.

Anal. Calcd. for $C_{11}H_8O_4S$: C, 55.92; H, 3.42; S, 13.58. Found: C, 55.97; H, 3.48; S, 13.38.

EXAMPLE 6

Sodium 6-Methoxy-1-oxo-1H-2-benzothiopyran-3-carboxylate

To a stirred suspension of 1.6345 g. (6.915 mM) of the carboxylic acid of Example 5 in 50 ml. of distilled water is added 0.5809 g. (6.915 mM) of sodium bicarbonate. After stirring at 25° for 2 hours, the solution is filtered and freeze-dried to give sodium 6-methoxy-1-oxo-1H-2-benzothiopyran-3-carboxylate as a white solid, m.p. >360°.

Anal. Calcd. for $C_{11}H_7NaO_4S$. 1-½ $H_2O$: C, 46.31; H, 3.54; S, 11.24. Found: C, 46.51; H, 3.59; S, 11.14.

EXAMPLE 7

5-(2-Carboxy-4-methoxybenzylidene)rhodanine

To a hot stirred solution of 0.90 g. (5.0 mM) of 5-methoxyphthalaldehydic acid and 0.67 g. (5.0 mM) of rhodanine in 4 ml. of acetic acid is added 1.35 g. (16.4 mM) of anhydrous sodium acetate. After refluxing 0.5 hour, the solid yellow mass is cooled, poured into water, and filtered to separate 5-(2-carboxy-4-methoxybenzylidene)rhodanine as a yellow solid.

EXAMPLE 8

7-Methoxy-1-oxo-1H-2-benzothiopyran-3-carboxylic acid

A solution of the benzylidenerhodanine of Example 7 in 18 ml. of 15% NaOH is refluxed for 0.75 hour and poured into dilute HCl, whereupon a yellow solid forms. The solid is collected and recrystallized from ethanol to give 7-methoxy-1-oxo-1H-2-benzothiopyran-3-carboxylic acid as pale yellow needles, m.p. 291°–292°.

Anal. Calcd. for $C_{11}H_8O_4S$: C, 55.92; H, 3.42; S, 13.58. Found: C, 55.90; H, 3.43; S, 13.48.

EXAMPLE 9

Sodium 7-methoxy-1-oxo-1H-2-benzothiopyran-3-carboxylate

To a stirred suspension of 2.0347 g. (8.613 mM) of 7-methoxy-1-oxo-1H-2-benzothiopyran-3-carboxylic acid in 50 ml. of distilled water is added 0.7236 g. (8.613 mM) of sodium bicarbonate. The resulting mixture is stirred at 25°–35° for 1.25 hours, filtered, and the filtrate freezedried to give sodium 7-methoxy-1-oxo-1H-2-benzothiopyran-3-carboxylate as a pale yellow solid, m.p. >350°.

Anal. Calcd. for $C_{11}H_7NaO_4S$. $H_2O$: C 47.83; H, 3.29; S, 11.61. Found: C, 48.17; H, 3.06; S, 11.19.

EXAMPLE 10

5-(2-Carboxy-3-methoxybenzylidene)rhodanine

To a stirred hot solution of 2.10 g. (11.65 mM) of 6-methoxyphthalaldehydic acid and 1.57 g. (11.75 mM) of rhodanine in 8 ml. of acetic acid is added 3.12 g. (38.1 mM) of sodium acetate. The resulting solution is refluxed 0.5 hour and then poured into ice water to give a tan precipitate. The solid is collected and partially air-dried to give 5-(2-carboxy-3-methoxybenzylidene)rhodanine as a tan solid.

EXAMPLE 11

8-Methoxy-1-oxo-1H-2-benzothiopyran-3-carboxylic acid

A solution of the benzylidenerhodanine of Example 10 in 46 ml. of 15% NaOH is refluxed for 0.75 hour, cooled, and poured into dilute HCl. The resulting tan precipitate is collected and air-dried. Two recrystallizations from methanol (charcoal) give 8-methoxy-1-oxo-1H-2-benzothiopyran-3-carboxylic acid as a pale yellow solid, m.p. 275° (dec.).

Anal. Calcd. for $C_{11}H_8O_4S$: C, 55.92; H, 3.42; S, 13.58. Found: C, 55.79; H, 3.44; S, 13.46.

EXAMPLE 12

Sodium 8-methoxy-1-oxo-1H-2-benzothiopyran-3-carboxylate

To a stirred suspension of 2.0221 g. (8.560 mM) of 8-methoxy-1-oxo-1H-2-benzothiopyran-3-carboxylic acid in 50 ml. of distilled water is added 0.7191 g. (8.560 mM) of sodium bicarbonate. The solid dissolves fairly rapidly and after stirring at 25° for 1 hour the solution is filtered and the filtrate freeze-dried to give sodium 8-methoxy-1-oxo-1H-2-benzothiopyran-3-carboxylate as a yellow solid, m.p. 307° (dec.).

Anal. Calcd. for $C_{11}H_7NaO_4S$. 1–3/4 $H_2O$: C, 45.59; H, 3.65; S, 11.07. Found: C, 45.58; H, 3.67; S, 11.12.

EXAMPLE 13

5-(2-Carboxy-α-methylbenzylidene)rhodanine

To a hot stirred solution of 2-carboxyacetophenone (1.91 g., 11.65 mM) and 1.57 g. (11.75 mM) of rhodanine in 8 ml. of acetic acid is added 3.12 g. (38.1 mM) of sodium acetate. The solution is refluxed for 3.5 hours, cooled, and poured into water, whereupon a gum forms. The gum crystallizes and is collected and recrystallized from methanol to give 5-(2-carboxy-α-methylbenzylidene) rhodanine as yellow-brown crystals, m.p. 193°–195°.

EXAMPLE 14

4-Methyl-1-oxo-1H-2-benzothiopyran-3-carboxylic acid

A stirred solution of 2.00 g. (7.17 mM) of the carboxylic acid of Example 13 in 15 ml. of 15% sodium hydroxide is refluxed for 0.75 hour, cooled, and poured into dilute hydrochloric acid, whereupon a precipitate forms. The solid is collected and recrystallized from ethyl acetate-hexane to give a tan solid. This solid is heated briefly to 245°, cooled, and the residue recrystallized from ethyl acetatehexane to give 4-methyl-1-oxo-1H-2-benzothiopyran-3-carboxylic acid as tan crystals, m.p. 247°–248°.

Anal. Calcd. for $C_{11}H_8O_3S$: C, 59.99; H, 3.67; S, 14.56. Found: C, 59.88; H, 3.68; S, 14.65.

EXAMPLE 15

Sodium 4-methyl-1-oxo-1H-2-benzothiopryan-3-carboxylate

To a stirred suspension of 2.0090 g. (9.122 mM) of 4-methyl-1-oxo-1H-2-benzothiopyran-3-carboxylic acid in 50 ml. of distilled water is added 0.7663 g. (9.122 mM) of sodium bicarbonate. After stirring at room temperature for 1.5 hours, the solution is filtered and the filtrate freeze-dried to give sodium 4-methyl-1-oxo-1H-2-benzothiopyran-3-carboxylate, m.p. 330° (dec.).

Anal. Calcd. for $C_{11}H_7NaO_3S$. 1/8 $H_2O$: C, 54.03; H, 2.98; S, 13.11. Found: C, 54.40; H, 3.04; S, 12.65.

EXAMPLE 16

5-(2-Carboxy-6-methoxybenzylidene)rhodanine

To a stirred hot solution of 0.45 g. (2.50 mM) of 3-methoxyphthalaldehydic acid and 0.34 g. (2.50 mM) rhodanine in 3 ml. of acetic acid is added 0.68 g. (8.2 mM) of anhydrous sodium acetate. The resulting solution is refluxed 1.5 hours, cooled, and poured into 40 ml. of water to give a yellow gum which slowly solidifies to a yellow solid. The solid is collected, washed with water, and air-dried to give 5-(2-carboxy-6-methoxybenzylidene)rhodanine.

EXAMPLE 17

5-Methoxy-1-oxo-1H-2-benzothiopyran-3-carboxylic acid

A solution of 0.6 g. (2 mM) of the benzylidenerhodanine of Example 16 in 10 ml. of 15% NaOH is refluxed under nitrogen for 0.5 hour, cooled, and poured into cold dilute HCl to form a tan precipitate. The solid is collected, washed with water and recrystallized from methanol to give 5-methoxy-1-oxo-1H-2-benzothiopyran-3-carboxylic acid as yellow needles, m.p. 283°–284°.

Anal. Calcd. for $C_{11}H_8O_4S$: C, 55.92; H, 3.42; S, 13.58. Found: C, 56.09; H, 3.38; S, 13.59.

We claim:

1. The method of inhibiting the release of spasmogens from antigen- antibody reactions in an animal susceptible to extrinsic asthma, hay fever, urticaria, eczema or atopic dermatitis which comprises administering to said animal a safe and effective anti-allergy amount of a compound of Formula I:

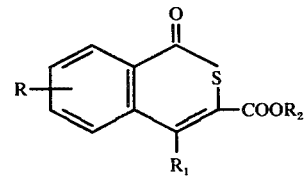

in which R is hydrogen or lower alkoxy of 1 to 4 carbon atoms, $R_1$ is hydrogen or a lower alkyl of 1 to 4 carbon atoms, and $R_2$ is hydrogen or sodium.

2. The method of claim 1 in which the compound administered is 1-oxo-1H-2-benzothiopyran-3-carboxylic acid.

3. The method of claim 1 in which the compound administered is sodium 1-oxo-1H-2-benzothiopyran-2-carboxylate.

4. The method of claim 1 in which the compound administered is sodium 6-methoxy-1-oxo-1H-2-benzothiopyran-3-carboxylate.

5. The method of claim 1 in which the compound is administered by inhalation.

6. The method of claim 1 in which the compound is administered orally.

7. A pharmaceutical composition for use in inhibiting the release of spasmogens from antigen-antibody reactions in animals susceptible to extrinsic asthma, hay fever, urticaria, eczema or atopic dermatitis which comprises an oral dosage form containing an effective amount of a compound of claim 1 in combination with pharmaceutical diluents.

8. The composition of claim 7 in the form of a tablet or capsule.

* * * * *